United States Patent [19]

Bartlett

[11] Patent Number: 4,767,774
[45] Date of Patent: Aug. 30, 1988

[54] SYNERGISTIC FUNGICIDAL COMPOSITION EMPLOYING SUBSTITUTED CARBOXAMIDOTHIAZOLES AND IMIDAZOLES

[75] Inventor: Digby H. Bartlett, Battenhall, England

[73] Assignee: Uniroyal Chemical Limited, Edinburgh, Scotland

[21] Appl. No.: 868,220

[22] Filed: May 28, 1986

[30] Foreign Application Priority Data

Jun. 5, 1985 [GB] United Kingdom ............... 8514217
Apr. 30, 1986 [GB] United Kingdom ............... 8610541

[51] Int. Cl.$^4$ ...................... A01N 43/50; A01N 43/78
[52] U.S. Cl. ..................................... 514/365; 514/399
[58] Field of Search ............................... 514/365, 399

[56] References Cited

U.S. PATENT DOCUMENTS 3,505,055 4/1970 von Schmeling et al. ......... 514/228

OTHER PUBLICATIONS

Cserjesi et al., C.A., vol. 84, (1976), 100690c.
Harrison et al., C.A., vol. 20, (1969), 87799j.

Primary Examiner—Allen J. Robinson
Attorney, Agent, or Firm—William E. Dickheiser

[57] ABSTRACT

Compositions comprised of (A) certain substituted carboxamidothiazoles and (B) one or more compounds selected from the group consisting of imidazoles, triazoles, guanadines, halonitrobenzenes, manganese and zinc salts of ethylene-bis(dithiocarbamate), pyrimidines, dicarboxamides, pyrrolidines and thiurams exhibit synergistic fungicidal activity. Also, a method for protecting plants from fungal disease comprising treating such plants with a fungicidally effective amount of said composition is disclosed.

8 Claims, No Drawings

SYNERGISTIC FUNGICIDAL COMPOSITION EMPLOYING SUBSTITUTED CARBOXAMIDOTHIAZOLES AND IMIDAZOLES

FIELD OF THE INVENTION

This invention relates to a synergistic fungicidal composition comprised of (A) certain substituted carboxamidothiazoles and (B) one or more compounds selected from the group consisting of imidazoles, triazoles, guanadines, halonitrobenzenes, manganese and zinc salts of ethylene-bis(dithiocarbamate), pyrimidines, dicarboxamides, pyrrolidines and thiurams. In another aspect, this invention relates to a method for protecting plants from fungal disease, which method involves treating such plants with a fungicidally effective amount of said composition.

BACKGROUND OF THE INVENTION

The need for effective protection of plants against fungal disease requires no amplification, the results of such fungal attack being well documented. However, in the past, many effective fungicides were mercury-based, and were thus toxic to warm-blooded animals.

Accordingly, several non-mercury-based fungicides have been developed. Thus, for example, U.S. Pat. No. 3,505,055 to von Schmeling et al discloses carboxamidothiazoles which are effective fungicides. Similarly, U.S. Pat. No. 3,658,813 to Godefroi et al shows fungicidal 1-[beta-aryl-beta-(R-oxy)-ethyl]imidazoles, while British Pat. No. 1,522,657 discloses dioxolan-substituted triazoles which exhibit fungicidal activity. Sarrett et al, in U.S. Pat. No. 3,017,415, show certain thiazolyl benzimidazoles which function as anthelmintics.

While the above compounds will function admirably as fungicides when employed alone, it has been unexpectedly found that when certain compounds of the latter three patents (along with certain other known compounds) are employed in conjunction with certain carboxamidothiazoles (some of which are disclosed in U.S. Pat. No. 3,505,055 and others of which are closely related compounds) the efficacy of such combinations is greater than that predicted for the mere addition of the compounds alone.

DESCRIPTION OF THE INVENTION

In one aspect, the present invention is directed to a fungicidal composition comprising:

(A) a compound of the formula:

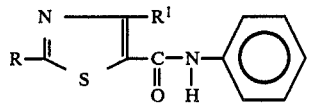

wherein R and R$^1$ are the same or different and are hydrogen or C$_1$-C$_8$ alkyl; and (B) one or more compounds selected from the group consisting of imidazoles, triazoles, guanadines, halonitrobenzenes, manganese and zinc salts of ethylene-bis(dithiocarbamate), pyrimidines, dicarboxamides, pyrrolidines and thiurams.

In another aspect, this invention relates to a method for protecting plants from fungal disease, which method comprises applying to such plants a fungicidally effective amount of a composition comprising:

(A) a compound of the formula:

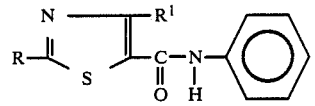

wherein R and R$^1$ are the same or different and are hydrogen or C$_1$-C$_8$ alkyl; and (B) one or more compounds selected from the group consisting of imidazoles, triazoles, guanadines, halonitrobenzenes, manganese and zinc salts of ethylene-bis(dithiocarbamate), pyrimidines, dicarboxamides, pyrrolidines and thiurams.

The carboxamidothiazoles which may be employed in the present invention are disclosed in U.S. Pat. No. 3,505,055 or are closely related thereto and are compounds of the formula:

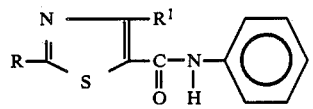

wherein R and R$^1$ may be the same or different and are hydrogen or C$_1$-C$_8$ alkyl.

More preferably, R and R$^1$ are each independently hydrogen or C$_1$-C$_4$ alkyl. Most preferably, R and R$^1$ are both methyl.

The imidazoles, triazoles, guanadines, halonitrobenzenes, manganese and zinc salts of ethylene-bis(dithiocarbamate), pyrimidines, dicarboxamides, or thiurams which comprise component (B) of the composition of the present invention are all known compounds having fungicidal activity.

Representative of the imidazoles which may be employed are 1-[2-(2,4-dichlorophenyl)-2-(2-propenyloxy)ethyl]-1H-imidazole, 1-N-propyl-N-[2-(2,4,6-trichlorophenoxy)ethyl]carbamoylimidazole, 1-[(2-[4-(4-bromophenoxy)phenyl]-1,3-oxathiolan-2-yl)methyl]-1H-imidazole, 1-[(2-[4-fluorophenyl]-1,3-oxathiolan-2-yl)methyl]-1H-imidazole, and 2-(4-thiazolyl)-1H-benzimidazole. Illustrative of the triazoles which may be employed are 1-[[2-(2,4-dichlorophenyl)-4-ethyl-1,3-dioxolan-2-yl]methyl]-1H-1,2,4-triazole, 1-[[2-(1,1'-biphenyl-4-yl)-1,3-oxathiolan-2-yl]methyl]-1H-1,2,4-triazole, 1-[[2-(4-fluorophenyl)-1,3-oxathiolan-2-yl]methyl]-1H-1,2,4-triazole, 1-[[2-(4-phenoxyphenyl)-1,3-dithiolan-2-yl]methyl]-1H-1,2,4-triazole, 1-[(2-[[(1,1'-biphenyl]-4-yl]-1,3-dithian-2-yl]methyl-1H-1,2,4-triazole, 1-[[2-[2-(1-, methyl ethoxy)phenyl]-1,3-oxathiolan-2-yl]methyl]-1H-1,2,4-triazole, 4-chlorobenzyl N-(2,4-dichlorophenyl)-2-(1,2,4-triazol-1-yl)ethanethioimidate and 2,4'-difluoro-alpha-(1H-1,2,4-triazole-1-ylmethyl)benzhydryl alcohol.

Representative of the guanadines which may be employed is 1,1'-iminobis(octamethylene)diguanadine, and illustrative of the halonitrobenzenes which may be employed is pentachloronitrobenzene.

Component (B) of the composition of this invention may comprise manganese, zinc or mixed manganese and zinc salts of ethylene-bis(dithiocarbamate).

Illustrative of the pyrimidines which may be employed are 5-butyl-2-ethylamino-6-methyl-4-(3H)-pyrimidinone and alpha-(2-chlorophenyl)-alpha-(4-fluorophenyl)-5-pyrimidine methanol. Representative of the dicarboxamides which may be employed is 3-(3,5-dichlorophenyl)-N-(1-methylethyl)-2,4-dioxo-1- imidazolidine carboxamide, while tetramethylthiuram is representative of the thiurams which may be employed.

Illustrative of the pyrrolidines which may be employed is 1-(3,5-dichlorophenyl)-3-methoxymethyl-2,5-pyrrolidindione.

Generally, the weight ratio of component (A) (i.e., the carboxamidothiazole) to component (B) present in the composition of this invention is preferably between about 1:5 and about 500:1. Typically, said weight ratio is generally more preferably between about 1:2 and about 200:1.

When component (B) is 1-[2-(2,4-dichlorophenyl)-2-(2-propenyloxy)ethyl]-1H-imidazole or 2-(4-thiazolyl)-1H-benzimidazole most preferably the weight ratio of component (A) to component (B) is between about 5:1 and about 75:1. When component (B) is 1-[[2-(2,4-dichlorophenyl)-4-ethyl-1,3-dioxolan-2-yl]methyl]-1H-1,2,4-triazole, most preferably the weight ratio of component (A) to component (B) is between about 25:1 and about 375:1. When component (B) is 4-chlorobenzyl N-(2,4-dichlorophenyl)-2-(1,2,4-triazol-1-yl)ethanethioimidate, most preferably the weight ratio of component (A) to component (B) is between about 1:2 and 10:1. The most preferred weight ratios for any particular set of components (A) and (B) may be readily determined by one skilled in the art utilizing conventional experimentation.

The composition of the present invention may further comprise one or more carrier materials such as talc, kaolin, bentonite and baryters, as well as stickers such as Spindeloil, ethylene glycol and polyvinylacetate. The composition may also include conventionally employed pigments such as iron oxide, Rubin Toner, titanium dioxide, and the like.

The compositions of this invention may be formulated as a powder by mixing together all the dry materials, including the carrier and additives until a homogenous mixture is formed. The stickers are then added and the whole mixed again until the mixture becomes essentially homogenous.

In the case of a liquid formulation, organic solvents such as xylene, dimethyl formamide, ethylene glycol, methanol and cyclohexane can be used as diluting agents and mixed together with surface active agents (such as, for example, calcium dodecylbenzenesulphonate, polyglycol ether and acrylopolyether alcohols) as well as a dye (such as Rhodamine, methylviolet and the like).

Moreover, the composition of this invention may be used together with one or more additional pesticidal materials such as insecticides, for instance organochlorine compounds such as Lindane and the like; organophosphoric esters such as Diazinon, Isazofos, Thiofanox and the like; and carbamates such as Carbofuran, Mercaptodimethar, Bendiocarb and the like; and repellants such as anthraquinone, thioanthraquinone, Benzathrone, Ziram and diphenylguanidine and the like in order to protect the plants against pests such as insects.

The method of this invention comprises applying to plants a fungicidally effective amount of the composition of this invention. Although the composition may be applied to any portion of the plants to be protected, the instant compositions are especially effective when employed as seed dressings.

When employed as seed dressings, preferably between about 5 grams and about 100 grams of composition is applied to each 100 kilograms of seed. More preferably, the composition is applied at a rate of between about 10 grams and about 50 grams per 100 kilograms of seed.

It is to be understood that the synergistic fungicidal control exhibited by the compositions of this invention is only exhibited wherein limited amounts of fungicide is employed—i.e., it is impossible to have synergy wherein the fungicides comprising this composition are used in such large amounts that essentially complete control would be expected employing either component alone. The essence of this invention is that lesser amounts of fungicide are necessary to obtain a given degree of control.

As is demonstrated in the examples below, the compositions of this invention exhibit unexpectedly enhanced, i.e., synergistic activity, rather than merely cumulative effect.

The compositions and method of this invention are useful in controlling a wide spectrum of fungi, such as *Calonectria nivalis, Pyrenophora graminea, Tilletia caries, Ustilago avenae Septoria nodorum, Tilletia foetida, Ustilago hordei, Ustilago nigra, Urocystis occulata, Ustilago nuda, Ustilago tritici, Typhula incarnate, Rhynchosporium secalis, Erysipha graminis* and the like, and demonstrate a high degree of activity against any certain seed pathogens, such as *Pyrenophora avenae, Cochliobolus savitus* and the like.

Moreover, the compositions of this invention are admirably suited for agricultural, horticultural and forestry applications because they are far less toxic to warm-blooded animals than mercury based fungicides.

EXAMPLES

The following Example are intended to further illustrate the invnetion and are not intended to limit the scope of the invention in any manner whatsoever.

Examples 1–9

In these Examples, the seed treatment method was carried out in accordance with the BBA guidelines 4-1.1 (March 1974) Ehle, H., Frohbeyer, P. E., Reinhard, H. and Roder, K. (1974), "Preliminary guidelines for the testing of seed dressings against cereal diseases", March 1974, published by BBA, Messeweg 11/12, 3300 Braunschweig. In this example, the following abbreviations represent the below listed compounds:

DMCI = 2,4-dimethyl-5-carboxanilidothiazole
DCPI = 1-[2-(2,4-dichlorophenyl)-2-(2-propenyloxy)ethyl]-1H-imidazole
TBIA = 2-(4-thiazolyl)-1H-benzimidazole
DCDT = 1-[[2-(2,4-dichlorophenyl)-4-ethyl-1,3-dioxolan-2-yl]methyl]-1H-1,2,4-triazole A wettable powder formulation was prepared using the following ingredients (all parts by weight):

| | |
|---|---|
| DMCI | 75.0 |
| Surfactants (*) | 4.1 |
| Rhodamine dye 3500 | 0.5 |
| Ethylene glycol | 3.0 |
| Dixie Clay | 17.4 |

(*) Mixture of alkali metal salts of alkyl naphthalene sulfonic acids: poly(ethylene oxide - propylene oxide).

Additional formulations were made up by dissolving the component (B) fungicides in dimethylformamide at the various concentrations (percent weight) indicated below (each formulation contained also 0.8% Rhodamine dye 3500):

| Fungicide | Concentrations |
|---|---|
| DCPI | 0.5 |
| TBIA | 0.5 |
| DCDT | 0.1 |

Spring wheat cv. Timmo was artificially infected with dry spores of *Tilletia caries at a rate of* 2 grams of spores per kilogram of wheat seed. The infected wheat seed was treated with various amounts each of the formulations above as summarized in Table I below. This treatment comprised diluting the above formulations with water and spraying a fine mist of the particular diluted formulation employed on the infected seeds using a deVilbiss [trademark] compressed air powered spray gun, followed by shaking the seed and chemical in a bottle for 5 minutes.

The seeds, which had been infected and treated as described above, were drilled into open ground, on a clay loam soil type, using a tractor mounted Oyjord Seed Drill. Plot size was 1.6 meters×5 meters with four replications, all treatments being fully radomized.

Assessment of fungicidal effect was carried out by taking 100 randomly selected heads per plot and examining for disease thus establishing the percent control of infection. The results of such testing are summarized in Table I, below.

TABLE I

| Experiment | A | B | C | D | E | F | G | H | I |
|---|---|---|---|---|---|---|---|---|---|
| DMCI | 37.5 | 75 | — | — | — | — | — | — | — |
| DCPI | — | — | 1 | 5 | — | — | — | — | — |
| TBIA | — | — | — | — | 1 | 3 | 5 | — | — |
| DCDT | — | — | — | — | — | — | — | 0.2 | 0.6 |
| Actual Control (Percentage) | 59.5 | 95.2 | 2.4 | 7.1 | 0 | 2.4 | 38.1 | 71.4 | 92.9 |

Employing the formulations and methods of treatment described in Experiments A-I above, several Experiments were conducted employing a mixture of compounds as summarized in Table II below. The expected control percentages were calculated for each Experiment employing the results of Experiments A-I utilizing the formula developed by S. R. Colby, "Calculating Synergistic and Antagonistic Responses of Herbicide Combinations", Weeds, Vol. 15, pp. 20-22 (1967), the disclosure of which is herein incorporated by reference.

The Colby formula may be summarized as follows:

If X=the percent inhibition of growth by herbicide

A at plb/A and Y=the percent inhibition of growth by herbicide

B at qlb/A and E=the expected percent inhibition of growth by herbicides

A+B at p+qlb/A then, $$E=X+Y-XY/100$$

When the observed response is greater than expected, the combination is synergistic; when less than expected, it is antagonistic. If the observed and expected responses are equal, the combination is additive.

The expected and actual control percentages for each Experiment are listed in Table II.

TABLE II

| Example No. | 1 | 2 | 3 | 4 | 5 | 6 | 7 | 8 | 9 |
|---|---|---|---|---|---|---|---|---|---|
| DMCI | 37.5 | 37.5 | 75 | 75 | 37.5 | 37.5 | 37.5 | 37.5 | 37.5 |
| DCPI | 1 | 5 | 1 | 5 | — | — | — | — | — |
| TBIA | — | — | — | — | 1 | 3 | 5 | — | — |
| DCDT | — | — | — | — | — | — | — | 0.2 | 0.6 |
| Control: | | | | | | | | | |
| Expected Percentage | 60.5 | 62.4 | 95.3 | 95.5 | 59.5 | 60.5 | 74.9 | 88.4 | 97.1 |
| Actual Percentage | 69 | 85.7 | 100 | 97.6 | 81 | 71.4 | 92.9 | 100 | 100 |

The data on Table II is clearly indicative of the synergistic fungicidal effects demonstrated by the compositions of the present invention wherein component (B) is an imidazole or a triazole.

Examples 10-15

The efficacy of several of the compositions of this invention in controlling *Fusarium nivale* was determined by the folloiwng process. Wheat seeds, infected with *F. nivale* were treated with the chemicals in the dosages listed in Table III in a seed treating machine. One hundred seeds for each treatment were placed between two sheets of water-soaked absorbent paper to provide moisture for seed germination. The blotter paper was then rolled loosely holding the seeds in the moist paper. The rolled blotters were then placed in a sealable plastic bag with 5 cm space left open at the top for proper air exchange. All the treatments were placed in separate bags in a cold chamber at 5° C. for 7 days. Untreated control bags were also done in the same manner. This temperature promoted development of the Fusarium disease. The bags were then removed and transferred to an illuminated incubator at 20° C. for another 7 days for further disease development. At the end of this period efficacy of control was determined by counting the numbers of infected seedlings from each treatment and tabulating the % diseased seedlings. These data were compared to that from untreated controls and the percentage reduction in disease (% control) was calculated for each treatment.

Moreover, the theoretical control for each combination was determined employing the Colby formula. The results of such testing are summarized in Table III.

TABLE III

| EXAMPLE | COMPOUND | CONCENTRATION (g/100 kg seed) | % CONTROL | THEORETICAL CONTROL | OBSERVED CONTROL |
|---|---|---|---|---|---|
| 10A | DMCI[1] | 18 | 30.8 | — | — |
| 10B | IODG[2] | 30 | 66.1 | — | — |
| 10 | DMCI | (18 g/100 kg) + IODG(30 g/100 kg) | | 76.54 | 86.1 |
| 11A | DMCI | 18 | 30.8 | — | — |
| 11B | PCNB[3] | 20 | 16.9 | — | — |
| 11 | DMCI | (18 g/100 kg) + PCNB(20 g/100 kg) | | 42.5 | 50.8 |
| 12A | DMCI | 18 | 30.8 | — | — |
| 12B | MNB[4] | 40 | 10.8 | — | — |
| 12 | DMCI | (18 g/100 kg) + MNB(40 g/100 kg) | | 38.3 | 50.8 |
| 13A | DMCI | 18 | 30.8 | — | — |
| 13B | IPRO[5] | 15 | 67.7 | — | — |
| 13 | DMCI | (18 g/100 kg) + IPRO(15 g/100 kg) | | 77.6 | 80.0 |
| 14A | DMCI | 18 | 30.8 | — | — |
| 14B | PROC[6] | 10 | 90.8 | — | — |
| 14 | DMCI | (18 g/100 kg) + PROC(10 g/100 kg) | | 93.6 | 100 |
| 15A | DMCI | 20 | 71.7 | — | — |
| 15B | CBDT[7] | 10 | 0 | — | — |
| 15 | DMCI | (20 g/100 kg) + CBDT(10 g/100 kg) | | 71.1 | 86.5 |

[1]DMCI = 2,4-dimethyl-5-carboxanilidothiazole
[2]IODG = 1,1'-iminobis(octamethylene) diguanadine
[3]PCMB = pentachloronitrobenzene
[4]MNB = manganese salt of ethylene-bis(dithiocarbamate)
[5]IPRO = 3-(3,5-dichlorophenyl)-N—(1-methylethyl)-2,4-dioxo-1-imidazolidine carboxamide
[6]PROC = 1-N—propyl-N—[2-(2,4,6-trichlorophenoxy)ethyl]carbamoyl-imidazole
[7]CBDT = 4-chlorobenzyl N—(2,4-dichlorophenyl)-2-(1,2,4-triazol-1-yl)ethanethioimidate

Examples 16–19

Employing the *Fusarium nivale* test employed in Examples 10–17, several combinations of 2,4-dimethyl-5-carboxanilidothiazole (DMCI) and 4-chlorobenzyl N-(2,4-dichlorophenyl)-2-(1,2,4-triazol-1-yl)ethanethioimidate (CBDT) were evaluated for their fungicidal efficacy. The results of such testing are summarized in Table IV.

The control observed for DMCI alone is as follows:

| Grams DMCI/100 kg seed | % control |
|---|---|
| 20 | 71.1 |
| 40 | 94.2 |

The control observed for CBDT alone is as follows:

| Grams CBDT/100 kg seed | % control |
|---|---|
| 10 | 0 |
| 20 | 28.8 |

TABLE IV

| Example | Grams DMCI per 100 kg seed | Grams CBDT per 100 kg seed | Theoretical % Control | Observed % Control |
|---|---|---|---|---|
| 16 | 20 | 10 | 71.10 | 86.5 |
| 17 | 20 | 20 | 79.42 | 94.2 |
| 18 | 40 | 10 | 94.20 | 100 |
| 19 | 40 | 20 | 95.88 | 100 |

The above results indicate the synergistic effect of a composition comprising DMCI and CBDT.

The above data indicate the unexpectedly superior control exhibited by the compositions of this invention relative to the control exhibited by either of the components alone.

What is claimed is:

1. A fungicidal composition comprising:
(A) a compound of the formula:

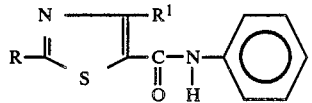

wherein R and R[1] are the same or different and are hydrogen or $C_1$-$C_8$ alkyl; and (B) an imidazole selected from the group consisting of 1-[2-(2,4-dichlorophenyl)-2-(2-propenyloxy)ethyl]-1H-imidazole, 1-N-propyl-N-[2-(2,4,6-trichlorophenoxy)ethyl]carbamoylimidazole and 2-(4-thiazolyl)-1H-benzimidazole;

wherein the weight ratio of compound (A) to compound (B) is between about 75:1 and about 1.8:1.

2. The fungicidal composition of claim 1 wherein R and R[1] are hydrogen or $C_1$-$C_4$ alkyl.

3. The fungicidal composition of claim 2 wherein R and R[1] are methyl.

4. The fungicidal composition of claim 1 wherein said imidazole is 2-(4-thiazolyl)-1H-benzimidazole.

5. The fungicidal composition of claim 4 wherein component (A) is 2,4-dimethyl-5-carboxanilidothiazole.

6. A method for protecting plants from fungal disease, which method comprises applying to such plants a synergistic, fungicidally effective amount of a composition comprising:

(A) a compound of the formula:

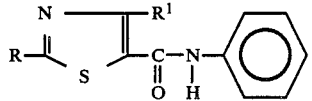

wherein R and R[1] are the same or different and are hydrogen or $C_1$-$C_8$ alkyl; and (B) an imidazole selected from the group consisting of 1-[2-(2,4-dichlorophenyl)-2-(2-propenyloxy)ethyl]-1H-imidazole, 1-N-propyl-N-[2-(2,4,6-trichlorophenoxy)ethyl]carbamoylimidazole and 2-(4-thiazolyl)-1H-benzimidazole;

wherein the weight ratio of compound (A) to compound (B) is between about 75:1 and about 1.8:1.

7. The method of claim 6 wherein said imidazole is 2-(4-thiazolyl)-1H-benzimidazole.

8. The method of claim 7 wherein component (A) is 2,4-dimethyl-5-carboxanilidothiazole.

* * * * *